United States Patent
Fujiyama et al.

(10) Patent No.: US 11,549,092 B2
(45) Date of Patent: Jan. 10, 2023

(54) CELL EVALUATION DEVICE AND CELL EVALUATION SYSTEM

(71) Applicants: Shimadzu Corporation, Kyoto (JP); Tokyo Institute of Technology, Tokyo (JP)

(72) Inventors: Yoichi Fujiyama, Kyoto (JP); Chikara Miyake, Kyoto (JP); Yoh-ichi Tagawa, Minato-ku (JP)

(73) Assignees: Shimadzu Corporation, Kyoto (JP); Tokyo Institute of Technology, Tokyo (JP)

( * ) Notice: Subject to any disclaimer, the term of this patent is extended or adjusted under 35 U.S.C. 154(b) by 82 days.

(21) Appl. No.: 16/689,820

(22) Filed: Nov. 20, 2019

(65) Prior Publication Data
US 2020/0157485 A1    May 21, 2020

(30) Foreign Application Priority Data
Nov. 21, 2018    (JP) .............................. JP2018-218390

(51) Int. Cl.
*B01L 3/00*    (2006.01)
*C12M 1/00*    (2006.01)

(52) U.S. Cl.
CPC ............. *C12M 29/04* (2013.01); *B01L 3/502* (2013.01); *C12M 45/07* (2013.01);
(Continued)

(58) Field of Classification Search
CPC ..... B01L 2300/0861; B01L 2300/0809; B01L 2300/0645; B01L 3/502; C12M 45/07; C12M 29/04
See application file for complete search history.

(56) References Cited

U.S. PATENT DOCUMENTS

| | | | |
|---|---|---|---|
| 2002/0022261 A1* | 2/2002 | Anderson | B01L 3/5027 435/287.2 |
| 2012/0190040 A1* | 7/2012 | Talebpour | C12M 23/16 435/7.1 |

(Continued)

FOREIGN PATENT DOCUMENTS

| | | |
|---|---|---|
| JP | 2007515958 A | 6/2007 |
| JP | 2008212006 A | 9/2008 |

(Continued)

OTHER PUBLICATIONS

Odijk et al., "Measuring direct current trans-epithelial electrical resistance in organ-on-a-chip microsystems", Lab on a chip, 15 (3), pp. 745-752 (2015).

(Continued)

*Primary Examiner* — Samuel P Siefke
*Assistant Examiner* — Tingchen Shi
(74) *Attorney, Agent, or Firm* — Muir Patent Law, PLLC

(57) ABSTRACT

A cell evaluation device includes: a porous membrane having a first main face and a second main face; a first passage having a first passage portion facing a first area on which cells are placed in the first main face of the porous membrane; a second passage having a second passage portion facing a second area in the second main face of the porous membrane, the second area being positioned backside of the first area; and a first electrode provided in the first passage portion and a second electrode provided in the second passage portion, the first electrode and the second electrode being positioned across the first area and the second area. In the cell evaluation device, tight junctions are formed among the cells by cell cultivation. With the cell evaluation device, any increase in the electric resistance occurring due to the formation of the tight junctions can be easily measured.

11 Claims, 4 Drawing Sheets

(52) U.S. Cl.
CPC ............. *B01L 2300/0645* (2013.01); *B01L 2300/0809* (2013.01); *B01L 2300/0861* (2013.01)

(56) References Cited

U.S. PATENT DOCUMENTS

| | | | | |
|---|---|---|---|---|
| 2012/0211373 | A1* | 8/2012 | El-Sayed | C12M 35/02 205/778 |
| 2013/0266979 | A1* | 10/2013 | Segerink | G01N 33/48707 435/29 |
| 2014/0065660 | A1 | 3/2014 | Kim et al. | |
| 2015/0301027 | A1 | 10/2015 | Charest et al. | |
| 2017/0089899 | A1* | 3/2017 | Kundrod | B01L 3/502761 |
| 2018/0221874 | A1* | 8/2018 | Parker | G01N 33/5064 |

FOREIGN PATENT DOCUMENTS

| | | |
|---|---|---|
| JP | 2017513483 A | 6/2017 |
| WO | 2005059088 A1 | 6/2005 |
| WO | 2012032646 A1 | 3/2012 |
| WO | 2015161087 A1 | 10/2015 |

OTHER PUBLICATIONS

First Office Action dated Mar. 15, 2022 issued for the corresponding Japanese Patent Application No. 2018-218390.
Akechi et al., Development of Liver-Functional Devices, Shimadzu Review 2010 vol. 67, No. 1, 2 pp. 53-59.
Notice of Allowance dated Oct. 4, 2022 issued for the corresponding Japanese Patent Application No. 2018-218390.
Chinese Office Action dated Dec. 5, 2022, issued for the corresponding Chinese Patent Application No. 201911151385.0.

* cited by examiner

CELL EVALUATION DEVICE AND CELL EVALUATION SYSTEM

TECHNICAL FIELD

The present invention relates to a cell evaluation device, and a cell evaluation system including the cell evaluation device, and in particular to a device to be used for checking the condition of tight junctions formed among cells while the cells are being cultivated.

BACKGROUND ART

Tight junctions are formed among epithelium cells to a great extent in a living body, and the tight-junctioned tissues sustain absorption, metabolism, and other important functions. Thus, it is necessary to confirm that the tight junctions are formed among cells before experiments for determining various functions. Intestinal epithelium cells form the internal surface of an intestinal tract of a living body. In the intestinal epithelium cells, the tight junctions are formed among cells adjacent to one another, thereby preventing the invasion of microorganisms and harmful substances into the living body. Medicines and foods for recovering the proper functions of the intestinal tract are developed by researching such intestinal epithelium cells (Patent Literature 1, for example).

In such developments, the intestinal epithelium cells are first cultivated to allow the tight junctions to be formed among the cells. Then, a target substance is caused to act on the intestinal epithelium cells among which the tight junctions are formed, and the change in the condition of the cells is observed. For such a series of processing, a cell culture insert has conventionally been widely used.

The cell culture insert is configured such that an insert is hung inside each well of a well plate. The bottom of the insert is formed of a porous membrane. In the cell culture insert, a first culture solution is put into the interior of the insert, a second culture solution is put between the insert and the well plate, and cells are cultivated on the porous membrane.

Then, electrodes of a resistance meter is inserted in the interior of the insert and between the insert and the well plate to measure the electric resistance. The electric resistance thus measured includes electric resistance of the porous membrane and electric resistance of the cells. After the cell cultivation starts, as the number of tight junctions formed among the cells increases, the electric resistance increases. When sufficient tight junctions are formed among the cells, the electric resistance does not further increase. Accordingly, when the measurement value of the electric resistance becomes substantially constant, it is determined that the sufficient tight junctions are formed among the cells. After the formation of the tight junctions among the cells is confirmed, a culture solution containing the target substance is introduced in place of the second culture solution, and the change in the condition of the cells is observed.

In recent years, a cell evaluation device on which an electrode is integrally mounted has been proposed (for example, Non Patent Literature 1). The cell evaluation device disclosed in Non Patent Literature 1 has a first passage member, and a second passage member, both of which are a substantially S-shaped tube, and a porous membrane. The first passage member and the second passage member are arranged to lie one over another crossing each other. The porous membrane is placed at the crossing point of a first passage formed inside the first passage member and a second passage formed inside the second passage member, so that the first passage and the second passage communicate with each other through the pores of the porous membrane. A first electrode is provided at an inlet of the first passage member, and a second electrode is provided at an outlet of the second passage member.

In the cell evaluation device, cells are cultivated on the porous membrane while the first culture solution flows through the first passage, and the second culture solution flows through the second passage. The electric resistance between the two electrodes is measured to check the condition of the tight junctions formed among the cells. After the formation of the sufficient tight junctions among the cells is confirmed, a culture solution containing the target substance is introduced instead of the first culture solution, and the change in the condition of the cells is observed.

CITATION LIST

Patent Literature

Patent Literature 1: JP 2008-212006 A

Non Patent Literature

Non Patent Literature 1: "Measuring direct current trans-epithelial electrical resistance in organ-on-a-chip microsystems", by Odijk M. et al., Lab on a chip, 15(3), 745-752 (2015)

SUMMARY OF INVENTION

Technical Problem

In the cell evaluation device according to Non Patent Literature 1, the first electrode is provided at the inlet of the first passage member, and the second electrode is provided at the outlet of the second passage member, as previously mentioned. The electric resistance between the two electrodes includes electric resistance of the first passage and the second passage, in addition to the electric resistance of the cells and the porous membrane. Accordingly, the difference in the electric resistance before and after the formation of tight junctions among the cells is relatively small. This makes it difficult to measure the increase in electric resistance occurring due to the formation of tight junctions among the cells.

An objective to be achieved by the present invention is to easily measure the increase in the electric resistance occurring due to the formation of tight junctions in a cell evaluation device in which the tight junctions are formed among the cells by the cultivation of the cells.

Solution to Problem

The present invention developed for achieving the previously described objective is a cell evaluation device including:

a porous membrane having a first main face and a second main face;

a first passage having a first passage portion facing a first area on which cells are placed in the first main face of the porous membrane;

a second passage having a second passage portion facing a second area in the second main face of the porous membrane, the second area being positioned backside of the first area; and a first electrode provided in the first passage portion and a second electrode provided in the second passage portion, the first electrode and the second electrode being positioned across the first area and the second area.

Advantageous Effects of Invention

In the cell evaluation device according to the present invention, the first electrode and the second electrode are respectively provided in the first passage portion and the second passage portion so as to be positioned across the first area on which cells are placed and the second area positioned backside of the first area. With this configuration, the influence of the electric resistance of passages other than the first passage portion facing the first area and the second passage portion facing the second area is reduced. Accordingly, the increase in the electric resistance occurring due to the formation of tight junctions among the cells during cell cultivation can be easily measured.

DESCRIPTION OF EMBODIMENTS

Figure 1:
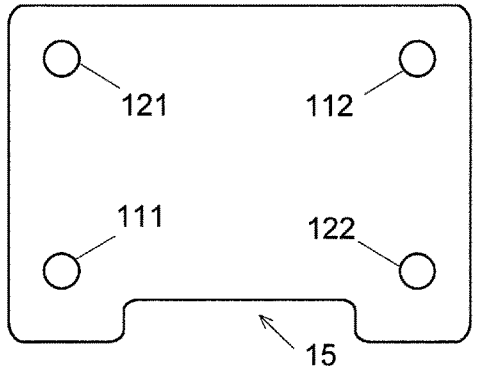
FIG. 1 shows the structure of each member constituting a cell evaluation device according to an embodiment of the present invention.
Figure 1:
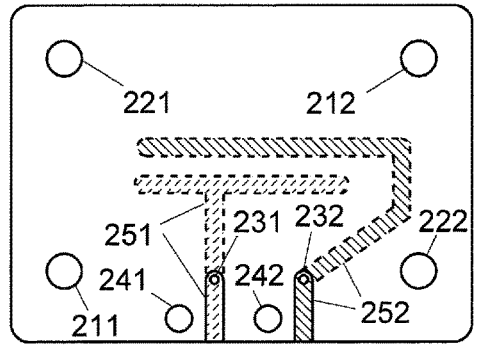
Figure 1:
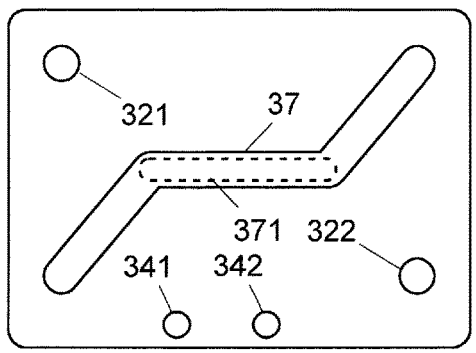
Figure 1:
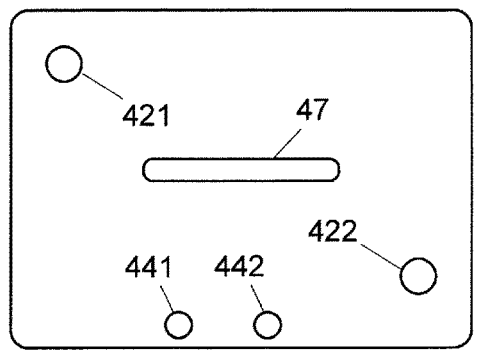
Figure 1:
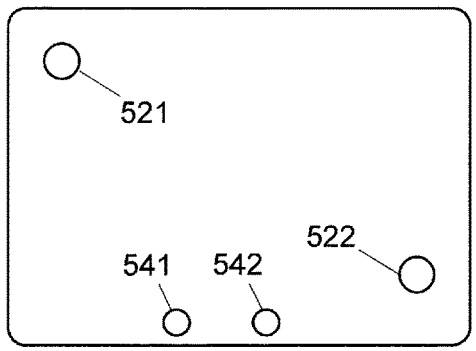
Figure 1:
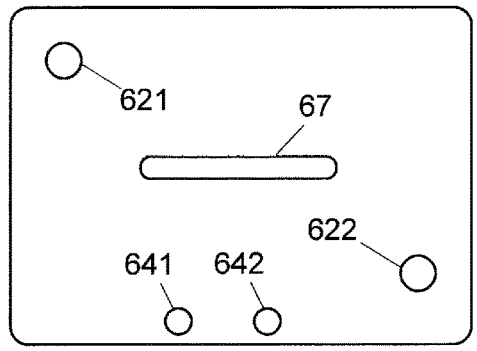
Figure 1:
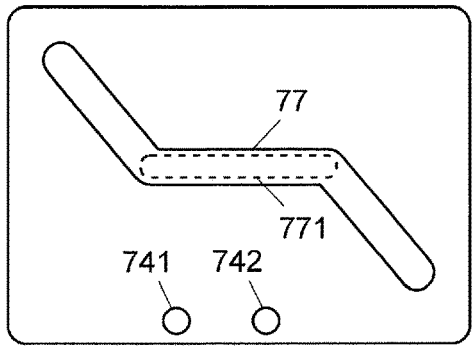
Figure 1:
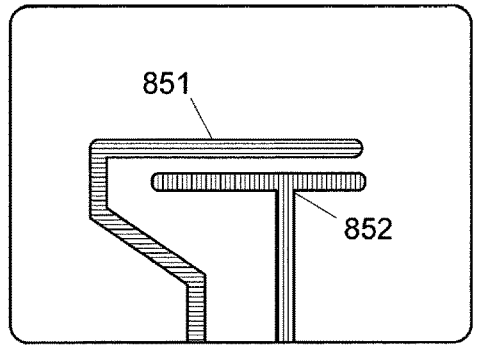

An embodiment of a cell evaluation device according to the present invention is described as follows, with reference to the drawings. The cell evaluation device according to the present embodiment is used for: cultivating cells on a membrane provided inside the cell evaluation device for forming tight junctions among the cells; allowing a culture medium containing bacteria to act on the cells after the sufficient tight junctions are formed; and then observing any changes in the cells. The cell evaluation device according to the present embodiment is placed inside an anaerobic chamber, and a culture medium containing oxygen is poured on the membrane face. With this configuration, the effects of intestinal bacteria to intestinal epithelium cells can be observed, for example.

The cell evaluation device 1 according to the present embodiment is composed of eight layered members. The eight members are: a lid member 10; an upper electrode member 20; an upper passage member 30; an upper filter pressing member 40; a filter member 50; a lower filter pressing member 60; a lower passage member 70; and a lower electrode member 80, in the order from the top to the bottom when used.

FIG. 1 shows the configuration of each of the members.

The lid member 10 is a plate member provided with an upper passage inlet hole 111, an upper passage outlet hole 112, a lower passage inlet hole 121, and a lower passage outlet hole 122. To each of these holes, a tube made of silicone rubber is attached. A cutout portion 15 is provided at a position where terminals of electrodes (described later) are positioned. The lid member 10 may be made of resin. The resin is polydimethylsiloxane (PDMS) resin, for example. One of the examples of such resin is SILPOT 184 (produced by Dow Corning Toray Co., Ltd).

The upper electrode member 20 includes an upper passage inlet hole 211, an upper passage outlet hole 212, a lower passage inlet hole 221, a lower passage outlet hole 222, an upper first-electrode introducing hole 231, an upper second-electrode introducing hole 232, a lower first-electrode terminal hole 241, and a lower second-electrode terminal hole 242. The upper electrode member 20 may be made of glass, and an example of the glass is Eagle XG (registered trademark of Corning Incorporated). The upper electrode member 20 has a thickness of 0.5 mm, for example.

An upper first electrode 251 has a T-shaped part and a linear part. The T-shaped part of the upper first electrode 251 is provided on the lower face of the upper electrode member 20, and the linear part is provided on the upper face of the upper electrode member 20 at a position corresponding to the cutout portion 15. The T-shaped part and the linear part of the upper first electrodes 251, which are respectively provided on the lower face and the upper face of the upper electrode member 20, are electrically connected via the upper first electrode introducing hole 231.

An upper second electrode 252 is provided on the lower face of the upper electrode member 20. The upper second electrode 252 has: a linear part which is parallel to the top linear portion of the T-shaped part of the upper first electrode 251; and a part extending from one end of the linear part to the upper second electrode introducing hole 232 around the upper first electrode 251. The upper second electrode 252 has another linear part provided on the upper face of the upper electrode member 20, at a position corresponding to the cutout portion 15. This linear part of the upper second electrode 252, and the aforementioned parts of the upper second electrode 252, which are provided on the lower face of the upper electrode member 20, are electrically connected via the upper second electrode introducing hole 232.

The holes of the upper electrode 20 are formed by lithography and sandblasting. Titanium and platinum are subjected to sputtering to form Pt/Ti (titanium coated by platinum) electrode with a titanium layer and a platinum layer respectively having the thickness of 0.1 μm and 0.2 μm, so as to form the upper first electrode 251 and the upper second electrode 252. For patterning the upper first electrode 251 and the upper second electrode 252, a metal mask is used.

An upper passage member 30 includes a lower passage inlet hole 321, a lower passage outlet hole 322, a lower first-electrode terminal hole 341, and a lower second-electrode terminal hole 342. For the upper passage member 30, a sheet made of silicone rubber may be used, for example. The thickness of such a sheet may be 0.2 mm, for example. An upper passage 37 is formed in the upper passage member 30. The upper passage 37 has a shape in which three straight lines are connected, and has one end positioned below the upper passage inlet hole 211 and the other end positioned below the upper passage outlet hole 212. The upper passage 37 has, for example, a size with the width of 3 mm and the length of 37 mm (the length of a linear passage in the center part is 14 mm, and the length of a side passage connected to each of the opposite ends of the linear passage in the center is 11.5 mm). The length of the linear passage in the center is defined by the distance between the intersections of the linear center passage and each of the side passages. Although the upper passage member 30 (and the upper filter pressing member 40, the lower filter pressing member 60, and the lower passage member 70, all of which are described later) is produced by machining with a cutting plotter in the present embodiment, other processing methods including laser processing may be used.

The upper filter pressing member 40 includes a lower passage inlet hole 421, a lower passage outlet hole 422, a lower first electrode terminal hole 441, and a lower second electrode terminal hole 442. For the upper filter pressing member 40, a sheet made of silicone rubber may be used, for example. The thickness of such a sheet may be 0.2 mm, for example. The upper filter pressing member 40 is provided with an opening 47 for defining a cell placement area 100 on the filter member 50, which will be described later, at a position corresponding to a part of the upper passage 37 (linear passage in the center part). The opening 47 has a size with the width of 2 mm and the length of 16 mm, for example.

The filter member 50 includes a lower passage inlet hole 521, a lower passage outlet hole 522, a lower first-electrode terminal hole 541, and a lower second-electrode terminal hole 542. For the filter member 50, a track-etched membrane (corresponding to the porous membrane of the present invention) may be used. The track-etched membrane is prepared by forming through holes (having an exemplary size of 5 μm) in a random manner in a membrane (having an exemplary thickness of 20 μm) made of polycarbonate. For the track-etched membrane, ipPORE (produced by ARBROWN CO., LTD) may be used, for example.

The lower filter pressing member 60 is made of material the same as that of the upper filter pressing member 40, and has a structure the same as that of the upper filter pressing member 40. In other words, the lower filter pressing member 60 is provided with a lower passage inlet hole 621, a lower passage outlet hole 622, a lower first-electrode terminal hole 641, and a lower second-electrode terminal hole 642. For the lower filter pressing member 60, a sheet made of silicone rubber may be used as well, for example. The thickness of such a sheet may be 0.2 mm, for example. Furthermore, an opening 67 for defining a passage part to be in contact with the cells is provided at a position corresponding to a part of the lower passage 77 which will be described later. The opening 67 has a size with the width of 2 mm and the length of 16 mm, for example.

A lower passage member 70 is provided with a lower first-electrode terminal hole 741 and a lower second-electrode terminal hole 742. For the lower passage member 70, a sheet made of silicone rubber may be used, for example. The thickness of such a sheet may be 0.2 mm, for example. In addition, the lower passage member 70 is provided with a lower passage 77 having a shape symmetrical to the upper passage 37. The lower passage 77 has a size with the width of 3 mm, and the length of 37 mm (the length of the linear passage in the center part is 14 mm, and the length of a side part connected to each of the opposite ends of the linear passage in the center part is 11.5 mm). The lower passage 77 has one end positioned below the lower passage inlet hole 621 and the other end positioned below the lower passage outlet hole 622.

In the upper face of the lower electrode member 80, a lower second electrode 852 is provided symmetrically to the upper first electrode 251 (T-shaped electrode), and a lower first electrode 851 is provided symmetrically to the upper second electrode 252 (the electrode provided in a manner of taking a roundabout route around the upper first electrode 251). The lower first electrode 851 and the lower second electrode 852 are the Pt/Ti electrode as well, and are respectively formed in the same manner as the upper first electrode 251 and the upper second electrode 252. The lower electrode member 80 may be made of glass, and an example of the glass is the Eagle XG, for example. The lower electrode member 80 has an exemplary thickness of 0.5 mm.

The filter member 50 is adhered to the upper filter pressing member 40 and the lower filter pressing member 60 by plasma processing or the like. After the upper and lower filter pressing members 40 and 60 is adhered to the filter member 50, a platform for cell adhesion is coated on the cell placement area formed on the filter member 50, depending on the necessity. The coating can be performed by dropping a collagen solution from the opening 47 of the upper filter pressing member 40 and drying the dropped collagen solution, for example.

The upper electrode member 20 and the lower electrode member 80 respectively is adhered to the upper passage member 30 and the lower passage member 70 by oxygen plasma processing. The upper passage member 30 is adhered to the upper filter pressing member 40, and the lower filter pressing member 60 is adhered to the lower passage member 70, respectively by oxygen plasma processing. Accordingly, the cell evaluation device according to the present embodiment can be obtained.

Figure 2:
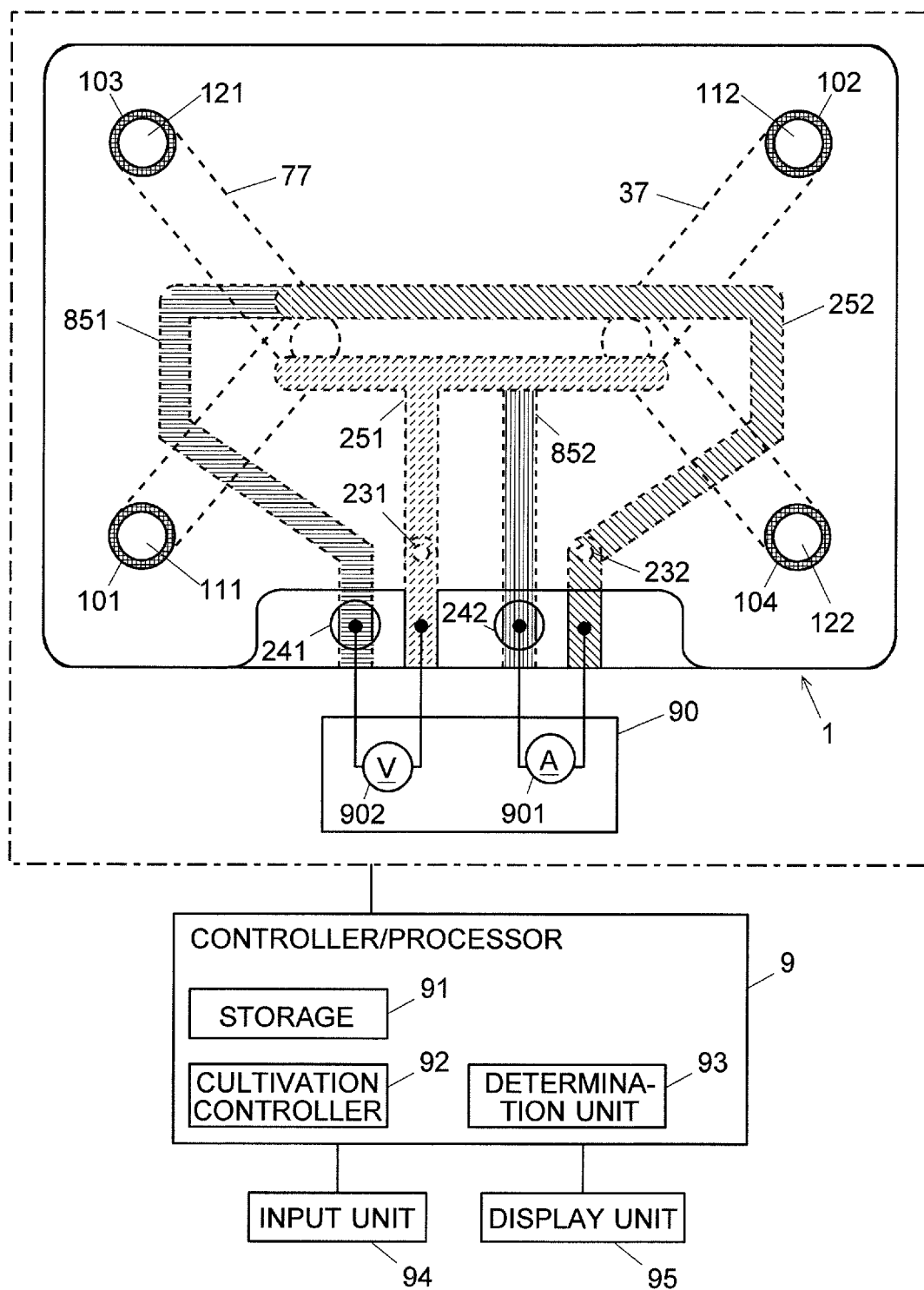
FIG. 2 is a schematic configuration diagram of a cell evaluation system including the cell evaluation device according to the present embodiment.

FIG. 2 is a schematic configuration diagram of a cell evaluation system including the cell evaluation device 1 thus produced, a later-described resistance meter 90, and a later-described controller/processor 9. In FIG. 2, the cell evaluation device 1 is illustrated in a plan view. In addition, FIG. 2 shows a state in which silicone rubber tubes 101 to 104 are respectively attached to the upper passage inlet hole 111, the upper passage outlet hole 112, the lower passage inlet hole 121, and the lower passage outlet hole 122, which are provided in the lid member 10. The portions indicated with broken lines are the configurations inside the cell evaluation device 1. In FIG. 2, in a case when a plurality of holes or members are positioned at the same position, only the members positioned at the top are associated with the reference numerals.

Figure 3:
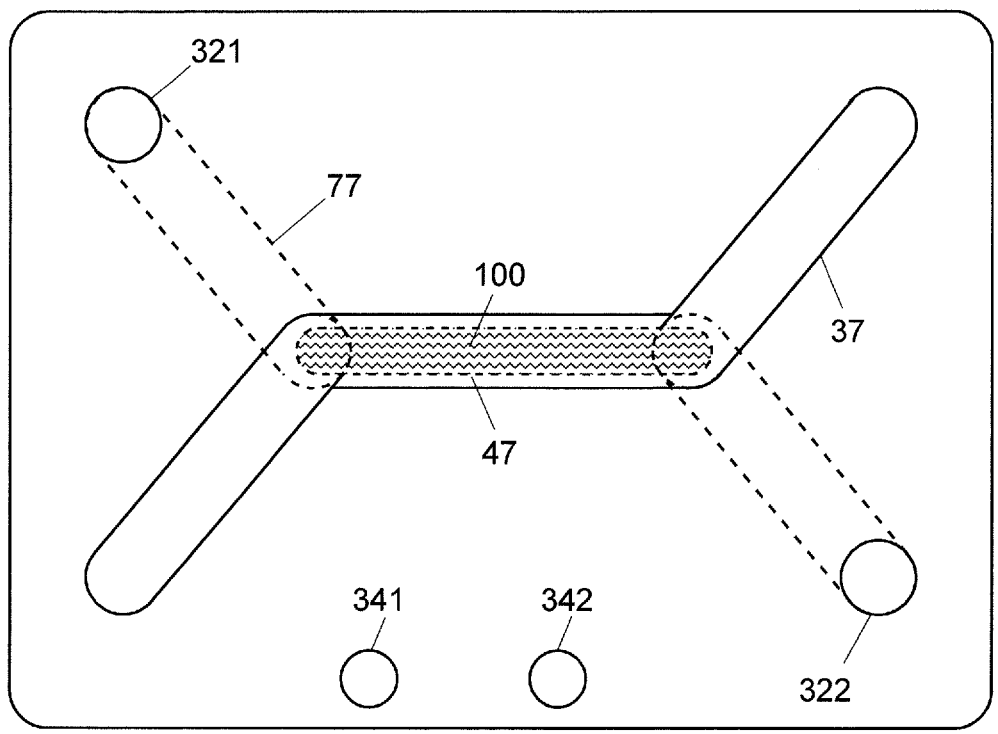
FIG. 3 is an explanatory diagram of a cell placement area formed inside the cell evaluation system according to the present embodiment.

In order to show the configuration inside the cell evaluation device 1, FIG. 3 shows a plan view of the state in which some parts of the cell evaluation device 1 (the passage member 30, the upper filter pressing member 40, the filter member 50, the lower filter pressing member 60, and the lower passage member 70) are superimposed. A cell placement area 100 is formed at a position where the opening 47 of the upper filter pressing member 40 is formed, on the upper face of the filter member 50 of the cell evaluation device 1, as shown with the hatching in FIG. 3. In FIG. 3, the configuration inside the cell evaluation device 1 is indicated by the broken lines, and only the members positioned at the top are associated with the reference numerals in a case when a plurality of holes or members are positioned at the same position.

As shown in FIG. 2, the upper first electrode 251 and the upper second electrode 252 are provided to cover a part of the upper area of a portion 371 (corresponding to the first passage part of the present invention) facing the cell placement area 100, in the upper passage 37 (corresponding to the first passage of the present invention). The lower first electrode 851 and the lower second electrode 852 are provided to cover, from the lower side, a part of a portion 771 (corresponding to the second passage part of the present invention) facing the lower face of the cell placement area 100, in the lower passage 77 (corresponding to the second passage of the present invention).

As shown in FIG. 2, the cell evaluation system according to the present invention includes the resistance meter 90 and the controller/processor 9, in addition to the cell evaluation device 1. The resistance meter 90 includes an ammeter 901 and a voltmeter 902, each of which has two terminals. Thus, the resistance meter 90 measures electric resistance by a four-terminal method.

The controller/processor 9 includes a cultivation controller 92 and a determination unit 93 as functional blocks, in addition to a storage 91. The controller/processor 9 actually works as a personal computer, and is connected by an input unit 94 and a display unit 95.

The procedure of the cell cultivation and the evaluation of the state of tight junctions formed among the cells, using the cell evaluation system according to the present embodiment, is described.

Terminals of the voltmeter 902 contained in the resistance meter 90 are respectively attached to a part of the upper first electrode 251, which is exposed from the cutout portion 15 of the lid member 10, and a part of the lower first electrode 851, which is exposed from the lower first-electrode terminal hole 241. Terminals of the ammeter 901 contained in the resistance meter 90 are respectively attached to a part of the upper second electrode 252, which is exposed from the cutout portion 15 of the lid member 10, and a part of the lower second electrode 852, which is exposed from the lower second-electrode terminal hole 242. In other words, each of the terminals is attached to measure the electric resistance between the upper second electrode 252 and the lower second electrode 852, by the four-terminal method. A pair of electrodes to which the terminals of the ammeter 901 are attached may be exchanged with a pair of electrodes to which the terminals of the voltmeter 902 are attached.

Then, the cell placement area 100 is coated by a cell fixing agent, and the cells to be cultivated are placed on the coated area.

When a user issues an instruction to start cultivation of the cells by performing the predetermined input operation through the input unit 94, the cultivation controller 92 causes a culture solution supplying unit (not shown) to introduce a first culture solution from the silicone rubber tube 101 to the upper passage 37 through the upper passage inlet holes 111 and 211. The first culture solution that has passed through the upper passage 37 passes through the upper passage outlet holes 212 and 112, and is discharged from the silicone rubber tube 102. A second culture solution is introduced in the lower passage 77 through the lower passage inlet holes 121, 221, 321, 421, 521 and 621 from the silicone rubber 103. The second culture solution that has passed through the lower passage 77 passes through the lower passage outlet holes 622, 522, 422, 322, 222 and 122, and is discharged from the silicone rubber tube 104.

The introduction of the first culture solution and the second culture solution causes cells on the cell placement area 100 to be cultivated, and thus tight junctions are formed among the cells. After the start of the cell cultivation, the determination unit 93 measures the electric resistance between the upper second electrode 252 and the lower second electrode 852 at the predetermined time intervals, and stores measurement values in the storage 91. In addition, the determination unit 93 causes the display unit 95 to display the change in the measurement values in the form of graph. The determination unit 93 determines whether a change ratio of the electric resistance (an increased amount of the electric resistance value per a predetermined time period) is lower than the predetermined change ratio, every time a new measurement value is obtained. When it is determined that the change ratio of the electric resistance is lower than the predetermined change ratio, the determination unit 93 causes the display unit 95 to display a message indicating that the cell cultivation is completed (sufficient tight junctions are formed among the cells).

When the message is indicated, the user checks the condition of the cells inside the cell placement area 100 from the upper side of the cell evaluation device 1. If the user determines that the sufficient tight junctions are formed among the cells, the user issues the instruction of terminating the cell cultivation by the predetermined input operation through the input unit 94. If the user determines that the tight junctions are not sufficiently formed among the cells, the user resets the determination results of the determination unit 93, and allows the device to continue the cell cultivation. In this case, the determination unit 93 repeats, once again, the operations described earlier.

Figure 4:
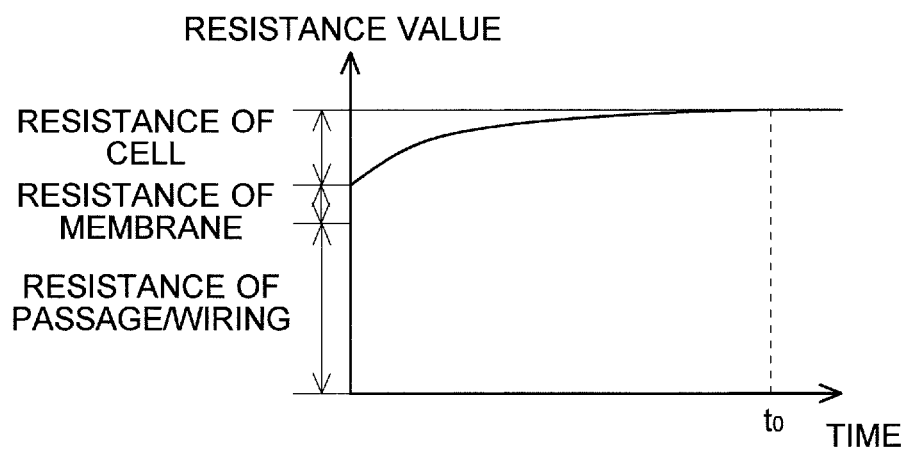
FIG. 4 is a graph showing the change in electric resistance in a conventional cell evaluation system.

In the conventional cell evaluation device proposed in Non Patent Literature 1, a first tubular passage member forming a first passage is provided in the upper side of the filter, a second tubular passage member forming a second passage was provided under the porous membrane, a pair of electrodes of a resistance meter are respectively attached to a passage inlet end of the first passage and a passage outlet end of the second passage, and the electric resistance is measured. Accordingly, the electric resistance between the two electrodes includes not only electric resistance of the cells and the porous membrane, but also electric resistance of the first and second passages and the electric resistance of a wiring (see FIG. 4). Thus, the difference in electric resistance before and after the formation of the tight junctions among the cells is relatively small. This makes it difficult to measure the increase in the electric resistance occurring due to the formation of the tight junctions among the cells. Thus, the time point (t0) at which the sufficient tight junctions are formed among the cells cannot be grasped.

Figure 5:
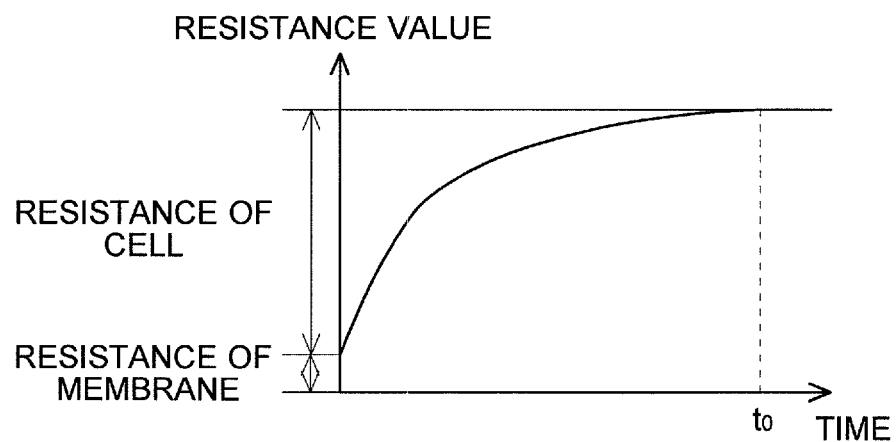
FIG. 5 is a graph showing the change in electric resistance in the cell evaluation system according to the present embodiment.

In the cell evaluation device 1 according to the present embodiment, a pair of electrodes 252 and 852 for measuring voltage are respectively placed at the outer periphery of a first passage portion 371 of the upper passage 37, which faces the cell placement area, and the outer periphery of a second passage portion 771 of the lower passage 77, which faces the cell placement area. In addition, each of the electrodes 251, 252, 851, and 852 has the length identical to or longer than the length in the longitudinal direction (the direction along which the upper passage 37 and the lower passage 77 extend) of the cell placement area 100. Accordingly, a current passage obliquely passing the cell placement area 100 of the filter member 50 is formed, and the voltage between the first passage portion 371 and the second passage portion 771 across the cell placement area 100 is measured. Such configuration eliminates the effect of the resistance components of the passages except the cell placement area 100. In a cell culture insert, the electric resistance is measured under the state where a well is filled with a culture solution. However, when a tiny amount of target cells is observed using a passage with the width at a level of 3 mm and the depth at a level of 0.2 mm, as in the present embodiment, the electric resistance in the passage may increase. Thus, the electric resistance is too large for a commercially available device to measure the electric resistance for some cases in the measurement using the passage having such a size. In contrast, the configuration according to the present embodiment is adopted, thereby adequately measuring the change in the electric resistance even with a passage having the width at a level of 3 mm and the depth at a level of 0.2 mm. As aforementioned, the measured electric resistance substantially contains only the electric resistance of the filter member 50 and cells inside the cell placement area 100 of the filter member 50 (see FIG. 5). Therefore, the increase in the electric resistance occurring due to the formation of the tight junctions among the cells can be easily measured.

The cell evaluation device 1 according to the present embodiment includes two pairs of electrodes (a pair of the upper first electrode 251 and the lower first electrode 851, and a pair of the upper second electrode 252 and the lower second electrode 852), and thus can measure the electric resistance by the four-terminal method. Accordingly, in the cell evaluation system including the cell evaluation device 1, the effect of the electric resistance of the wiring of the resistance meter is inhibited, and thus the increase in the electric resistance occurring due to the formation of the tight junctions among the cells can be easily measured.

In the cell evaluation device 1 according to the present embodiment, the exemplary measurement value of the electric resistance in the state where the upper passage 37 and the lower passage 77 are filled with a culture medium (10% of FSB in DMEM) is at a level of 2500 g. When caco-2 cells (cells derived from human colon cancer) are cultivated using this culture medium, the increase in the electric resistance occurring due to the formation of the tight junctions among the caco-2 cells can be confirmed. Meanwhile, in the cell evaluation device having the configuration that an electrode is provided at the end of the passage in the same manner as in the conventional device, the resistance value at the time point when the culture medium is filled is too high to measure the increase in the electric resistance value due to the formation of the tight junctions among the caco-2 cells.

In the cell evaluation device 1 according to the present embodiment, the upper first electrode introducing hole 231 and the upper second electrode introducing hole 232 are formed on the upper electrode member 20, and a part of each of the upper first electrode 251 and the upper second electrode 252 is exposed from the upper face of the cell evaluation device 1. In addition, the lower first-electrode terminal holes (241 and so on) and the lower second-electrode terminal holes (242 and so on) are provided in the respective members, and a part of each of the lower first electrode 851 and the lower second electrode 852 is exposed from the upper face of the cell evaluation device 1. With this configuration, every electrode can be contacted from the top of the cell evaluation device 1.

In the cell evaluation device 1 according to the present embodiment, the upper first electrode 251 and the upper second electrode 252 are configured to have a size and to be positioned so as to not cover the entirety of the cell placement area 100. In other words, two electrodes 251 and 252 are provided so that the cell placement area 100 can be visible in a plan view from the first passage portion 371. Therefore, the condition of the cells can be visually checked while the electric resistance values are measured, during the cell cultivation.

The aforementioned embodiment is an example of the present invention, and can be appropriately modified according to the objectives of the present invention.

The cell evaluation system according to the present embodiment can be widely used for evaluating not only the intestinal epithelium cell but also cells for which the formation of the tight junctions is necessary. Although Pt/Ti electrodes are used in the before-mentioned embodiment, cells inside the cell placement area 100 can be observed by using a transparent electrode, such as ITO.

Various embodiments according to the present invention are described in detail heretofore, with reference to the drawings, and various aspects of the present invention are to be described in closing. The reference numerals allocated to the respective elements do not limit the configuration of the present invention, but just expedites the understanding.

The cell evaluation device (1) of the first aspect of the present invention includes:

a porous membrane (50) having a first main face and a second main face;

a first passage (37) having a first passage portion (371) facing a first area (100) on which cells are placed in the first main face of the porous membrane (50);

a second passage (77) having a second passage portion (771) facing a second area in the second main face of the porous membrane (50), the second area being positioned in the backside of the first area (100); and a first electrode (252) provided in the first passage portion (371) and a second electrode (852) provided in the second passage portion (771), the first electrode (252) and the second electrode (852) being positioned across the first area (100) and the second area.

In the cell evaluation device according to the first aspect, the first electrode and the second electrode are respectively provided in the first passage portion and the second passage portion to be positioned across the first area on which the cells are placed and the second area positioned in the backside of the first area. Only the electric resistance of each of these portions is measured. Therefore, the increase in the electric resistance occurring due to the formation of the tight junctions among the cells during the cell cultivation can be easily measured.

In the cell evaluation device (1) of the second aspect of the present invention, in view of the cell evaluation device (1) of the first aspect, the first passage portion (371) and the second passage portion (771) are provided along the first area to extend in a substantially same direction, and in the direction, the length of the first electrode (252) is half or more of the length of the first area (100), and the length of the second electrode (852) is half or more of the length of the second area.

The pace of the formation of the tight junctions among the cells is not necessarily limited to be uniform over the entirety of the first area (cell placement area). For example, if the electrodes are locally placed at positions where the formation of the tight junctions among the cells proceeds quickly, the electric resistance may increase even though the sufficient tight junctions are not formed among the cells at a position far away from the electrodes. However, the cell evaluation device of the second aspect is used, thereby accurately measuring the change in electric resistance according to the condition in the formation of the tight junctions in the entire cell placement area, even when the formation pace of the tight junctions is not uniform. It should be noted that the first area is not limited to the linear shape as in the aforementioned embodiment, but may be curved or bent. The first passage portion and the second passage portion are not limited to the linear shape either as in the aforementioned embodiment, but may be curved or bent. If the first passage portion and the second passage portion are curved or bent, the curvature is not required to be uniform. In the present embodiment, each of the first passage portion and the second passage portion has a shape elongated in the width direction of the first passage and the second passage. However, this is the not the necessary requirement. The first passage portion (or the second passage portion) may be provided at a part of the first passage (or the second passage portion) in the width direction.

In the cell evaluation device (1) of the third aspect of the present invention, in view of the cell evaluation device (1) of the first aspect or the second aspect, the first electrode (252) is provided so that the first area (100) is visible in a plan view from the first passage portion (371).

The cell evaluation device of the third aspect is used, thereby visually confirming that the condition where the tight junctions are formed among the cells on the cell placement area. This is also embodied by using the electrode having the length shorter than the length (width) of the first area in the direction orthogonal to the direction along the first passage, for example. Furthermore, this is also embodied by placing the first electrode on at least a position where the first electrode does not cover a part of the first area, in the plan view from the outside of the first passage member.

In the cell evaluation device (1) of the fourth aspect of the present invention, in view of the cell evaluation device (1) of any one of the first aspect to the third aspect, the first electrode (252) is a transparent electrode.

In the cell evaluation device of the fourth aspect, the flexibility with respect to the position of the electrode is higher in comparison with the case where opaque electrodes are used.

The cell evaluation device (1) of the fifth aspect of the present invention, in view of the cell evaluation device (1) of any one of the first aspect to the fourth aspect, includes a third electrode (251) provided in the first passage portion (371) and a fourth electrode (851) provided in the second passage portion (771), so as to be positioned across the first area (100) and the second area.

The cell evaluation device of the fifth aspect is configured to measure the electric resistance by a so-called four-terminal method, using two pairs of electrodes (a pair of the first electrode and the second electrode, and a pair of the third electrode and the fourth electrode) as the electrode for being connected to an ammeter and the electrode for being connected to a voltmeter. In a conventional cell evaluation device, the electric resistance is measured by a so-called two-terminal method, and the electric resistance obtained by this method contains the resistance of wiring. Accordingly, the difference in electric resistance before and after the formation of the tight junctions among the cells is relatively small due to the wiring resistance. On the other hand, in the cell evaluation device of the fifth aspect, the electric resistance is measured by the four-terminal method. Thus, the influence by the wiring resistance to the measurement value is inhibited. Accordingly, the increase in the electric resistance occurring due to the formation of the tight junctions among cells during the cell cultivation can be further easily measured.

In the cell evaluation device (1) of the sixth aspect of the present invention, in view of the cell evaluation device (1) of any one of the first aspect to the fifth aspect, the first area (100) is defined by an opening (47) provided in the cell placement area definition member (40) fixed to the first main face of the porous membrane (50);

the first passage (37) is defined by an opening (37) provided in the first passage member (30) fixed to a face of the cell placement area definition member (40), the face being opposite to a face to which the porous membrane (50) is fixed;

the first electrode (252) is formed at the position facing the first area (100) in the first electrode member (20) fixed in a side opposite to the porous membrane (50), with respect to the first passage member (30);

the second passage (77) is defined by an opening (77) provided in the second passage member (70) fixed in a side opposite to the cell placement area definition member (40) with respect to the porous membrane (50);

the second electrode (852) is formed at a position facing the second area in the second electrode member (80) fixed in a side opposite to the porous membrane (50) with respect to the second passage member (70); and the entirety of the cell evaluation device is formed in a chip shape.

In the cell evaluation device of the sixth aspect, the cell placement area definition member, the first passage member, and the first electrode member are placed in one side of the porous membrane, and the second passage member and the second electrode member are placed in the other side of the porous membrane. The entirety of the cell evaluation device is formed in a chip shape. Accordingly, the handling of such a cell evaluation device is easier in comparison with a configuration in which the respective units are separately provided.

In the cell evaluation device (1) of the seventh aspect of the present invention, in view of the cell evaluation device (1) of the sixth aspect, the second area is defined by an opening (67) provided in the member (60) fixed to the second main face of the porous membrane (50).

In the cell evaluation device of the seventh aspect, the second passage is defined by the face of the porous membrane and the opening of the second passage member provided adjacent to the porous membrane. Accordingly, it is required to use the porous membrane having a size that can cover at least the entirety of the second passage. Meanwhile, in the cell evaluation device of the seventh aspect, the second passage is defined by the face of the porous membrane and the opening of the second passage member provided adjacent to the porous membrane. Accordingly, the porous membrane having a size that covers only the first area can be used. For the second passage member, a sheet made of silicone rubber is used as mentioned in the embodiment, for example. If the cell evaluation device of the sixth aspect does not include the member (60), the second passage is defined by adhering the silicone rubber sheet and the porous membrane. Although it is easy to adhere the silicone rubber sheets to each other, it is significantly difficult to adhere the porous membrane with the silicone rubber sheet. The configuration of the cell evaluation device of the seventh aspect is adopted, thereby accurately defining the second passage to easily embody the necessary functions.

In the cell evaluation device (1) of the eighth aspect of the present invention, the first electrode (252) and the second electrode (852) are both configured to be contactable from one side of the cell evaluation device (1).

In the cell evaluation device of the eighth aspect, the first electrode and the second electrode are contactable from one side of the cell evaluation device. This allows the electrodes to be easily connected by the terminal of the resistance meter.

The ninth aspect of the present invention is a cell evaluation system that includes:

the cell evaluation device (1) of the fifth aspect; and a resistance meter (90) including an ammeter (901) and a voltmeter (902), the ammeter (901) having two terminals respectively attached to the first electrode (252) and the second electrode (852), the voltmeter (902) having two terminals respectively attached to the third electrode (251) and the fourth electrode (851).

In the cell evaluation system according to the ninth aspect, the electric resistance of the cells and so on cultivated in the first area is measured by the four-terminal method. Accordingly, the influence of the wiring resistance to the measurement value is inhibited. Accordingly, in the cell evaluation system of the ninth aspect, the increase in the electric resistance occurring due to the formation of the tight junctions among the cells during cell cultivation can be easily measured, from the change in the measurement value.

REFERENCE SIGNS LIST

1 . . . Cell Evaluation Device
100 . . . Cell Placement Area
10 . . . Lid Member
15 . . . Cutout Portion
20 . . . Upper Electrode Member
251 . . . Upper First Electrode
252 . . . Upper Second Electrode
30 . . . Upper Passage Member
37 . . . Upper Passage
371 . . . Part of Upper Passage, Facing Cell Placement Area (First Passage Portion)
40 . . . Upper Filter Pressing Member
47 . . . Opening
50 . . . Filter Member
60 . . . Lower Filter Pressing Member
67 . . . Opening
70 . . . Lower Passage Member
77 . . . Lower Passage
771 . . . Part of Lower Passage, Area Facing Backside of Cell Placement Area (Second Passage Portion)
80 . . . Lower Electrode Member
851 . . . Lower First Electrode
852 . . . Lower Second Electrode
90 . . . Resistance Meter
9 . . . Controller/Processor
91 . . . Storage
92 . . . Cultivation Controller
93 . . . Determination Unit
94 . . . Input Unit
95 . . . Display Unit

The invention claimed is:

1. A cell evaluation device comprising:
   a porous membrane having a first main face and a second main face opposite to the first main face;
   a first passage member stacked on the first main face of the porous membrane in a first direction perpendicular to the first main face and the second main face, the first passage member having a first passage portion overlapping, in the first direction, a first area on which cells are placed in the first main face of the porous membrane, where the first area is a two-dimensional area having a longitudinal direction and a lateral direction, and the first passage portion extends along the longitudinal direction of the first area;
   a second passage member stacked on the second main face of the porous membrane in the first direction, the second passage member having a second passage portion formed within the second passage member, the second passage portion overlapping, in the first direction, a second area which is located on an opposite side of the first area across the porous membrane and is a two-dimensional area having a longitudinal direction and a lateral direction, where the second passage portion extends along the longitudinal direction of the second area;
   a first electrode member provided on a side of the first main face of the porous membrane;
   a second electrode member provided on a side of the second main face of the porous membrane; and
   a first electrode pair having a first electrode and a second electrode and a second electrode pair having a third electrode and a fourth electrode, where the first electrode pair and the second electrode pair are configured to measure an electric characteristic in accordance with a formation of tight junctions among the cells,
   wherein
   the first and third electrodes are arranged on the first electrode member along the longitudinal direction of the first area to overlap with the first passage portion,
   the second and fourth electrodes are arranged on the second electrode member along the longitudinal direction of the second area to overlap with the second passage portion,
   the first electrode and the second electrode are provided such a manner that the first electrode and the second electrode sandwich the first and second areas, and the third and fourth electrodes are provided such a manner that the third and fourth electrodes sandwich the first and second areas.

2. The cell evaluation device according to claim 1, wherein
   the first electrode and the third electrode are arranged on the first electrode member along the longitudinal direction of the first area such a manner that the first electrode and the third electrode cover the first passage portion, and
   the second electrode and the fourth electrode are arranged on the second electrode member along the longitudinal direction of the second area such a manner that the second electrode and the fourth electrode cover the second passage portion.

3. The cell evaluation device according to claim 1, wherein
   the first electrode and the third electrode are provided so that the first area is visible in a plan view from the first passage portion.

4. The cell evaluation device according to claim 1, wherein
   the first electrode is a transparent electrode.

5. The cell evaluation device according to claim 1, wherein
   the first area is defined by an opening provided in a cell placement area definition member, the cell placement area definition member being fixed to the first main face of the porous membrane;
   the first passage portion is defined by an opening provided in the first passage member, the first passage member being fixed to the cell placement area definition member;
   the first electrode is formed in a first electrode member, the first electrode member being fixed to the first passage member;
   the second passage portion is defined by an opening provided in the second passage member; and
   the second electrode is formed in a second electrode member, the second electrode member being fixed to the second passage member.

6. The cell evaluation device according to claim 5, wherein
the second area is defined by an opening provided in a pressing member fixed to the second main face of the porous membrane.

7. The cell evaluation device according to claim 1, wherein
the first electrode, the second electrode, the third electrode, and the fourth electrode are both formed in a manner of being contactable from one side of the cell evaluation device.

8. A cell evaluation system, comprising:
the cell evaluation device according to claim 1; and
a resistance meter including an ammeter and a voltmeter, the ammeter having two terminals respectively attached to the first electrode and the second electrode, and the voltmeter having two terminals respectively attached to the third electrode and the fourth electrode.

9. The cell evaluation device according to claim 5, wherein
an entirety of the cell evaluation device has a chip shape.

10. The cell evaluation device according to claim 6, wherein
the second passage member is fixed to the pressing member.

11. A cell evaluation device comprising:
a porous membrane having a first main face and a second main face opposite to the first main face;
a first passage member stacked on the first main face of the porous membrane in a first direction perpendicular to the first main face and the second main face, the first passage member having a first passage portion overlapping, in the first direction, a first area on which cells are placed in the first main face of the porous membrane;
a second passage member stacked on the second main face of the porous membrane in the first direction, the second passage member having a second passage portion formed within the second passage member, the second passage portion overlapping, in the first direction, a second area;
a first electrode member including a first electrode and a third electrode, the first electrode member fixed to the first passage member such that portions of the first electrode and third electrode are positioned across the first area and extend parallel with respect to each other; and
a second electrode member including a second electrode and a fourth electrode, the second electrode member fixed to the second passage member such that portions of the second electrode and the fourth electrode are positioned across the second area and extend parallel with respect to each other,
wherein the first electrode, the second electrode, the third electrode, and the fourth electrode are configured to measure an electric characteristic in accordance with a formation of tight junctions among the cells.

* * * * *